United States Patent [19]

Ball

[11] 4,315,448

[45] Feb. 16, 1982

[54] HYPODERMIC NEEDLE DESTRUCTOR

[76] Inventor: Edward W. Ball, 3418 Sleepy Hollow, Wichita, Kans. 67208

[21] Appl. No.: 172,968

[22] Filed: Jul. 28, 1980

[51] Int. Cl.³ .................. B23D 15/04; B23D 21/06
[52] U.S. Cl. ................................ 83/167; 83/580; 83/925 R
[58] Field of Search ............. 83/580, 925 R, 167, 83/199, 196; 225/93, 1

[56] References Cited

U.S. PATENT DOCUMENTS

| 338,396 | 3/1886 | Fitts | 83/580 |
| 415,621 | 11/1889 | Collins | 83/580 |
| 3,683,733 | 8/1972 | Johan et al. | 83/580 X |
| 3,785,233 | 1/1974 | Robinson | 83/580 X |
| 3,808,924 | 5/1974 | Ferguson | 83/199 |
| 4,255,996 | 3/1981 | Choksi et al. | 83/580 X |

*Primary Examiner*—Frank T. Yost
*Attorney, Agent, or Firm*—Edward L. Brown, Jr.

[57] ABSTRACT

A shearing device for disposable syringes which cuts off the needle with a cam-actuated knife blade. The syringe is inserted through an opening in the center of a rotating knob which knob is in turn connected to the knife blade, so that as the knob is rotated, the blade pivots against the base plate and shears off the needle extending through the opening in the handle, collecting the sheared needles in a receptacle box.

8 Claims, 7 Drawing Figures

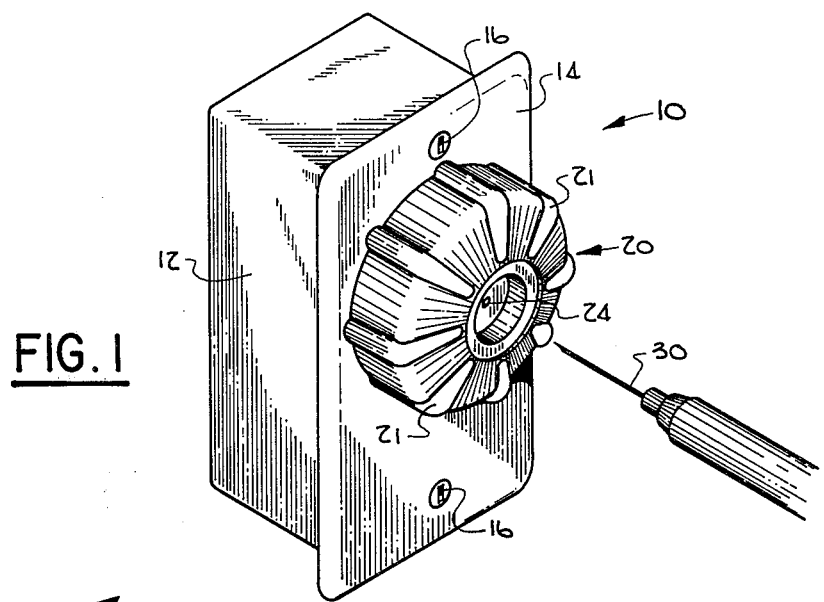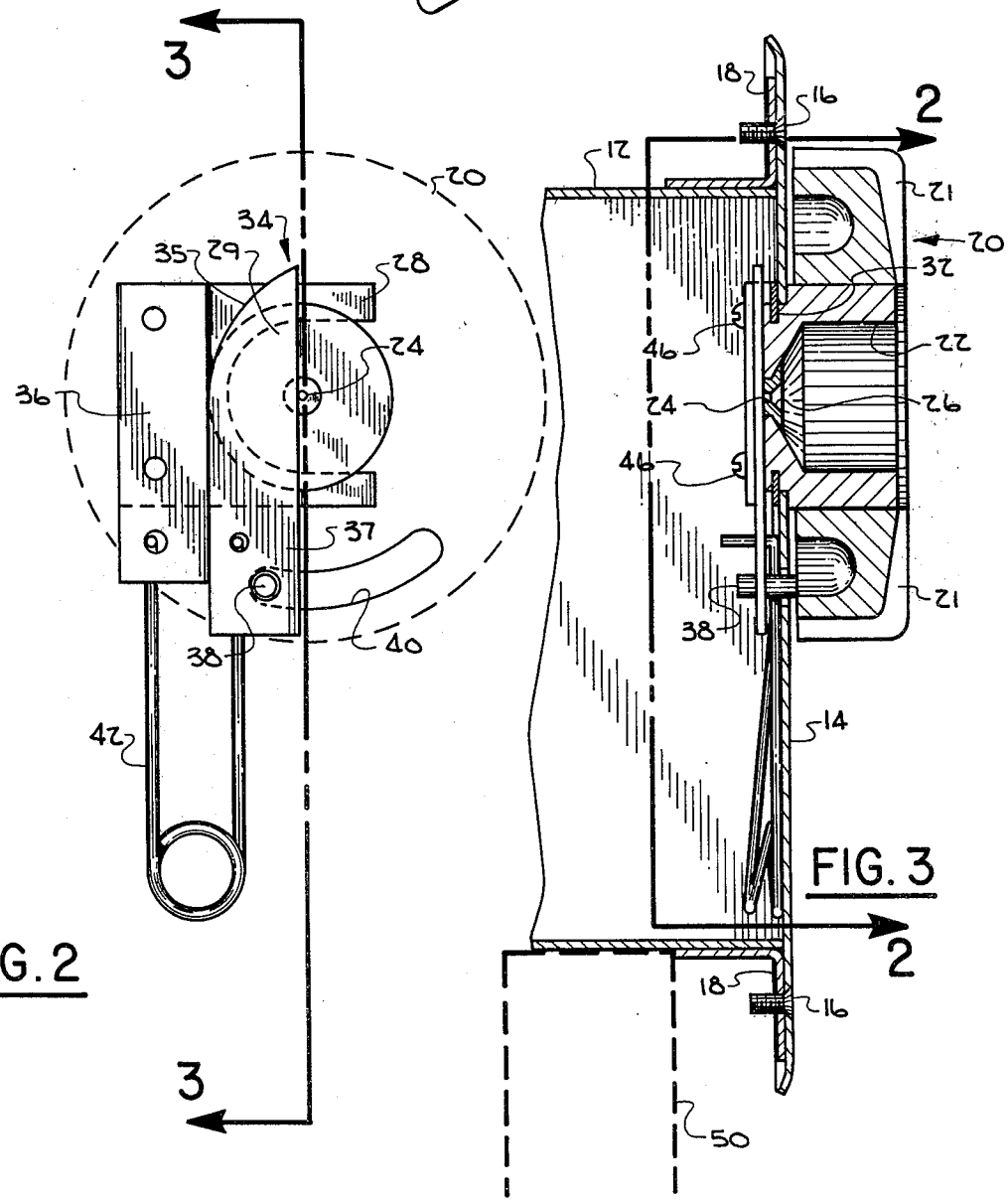

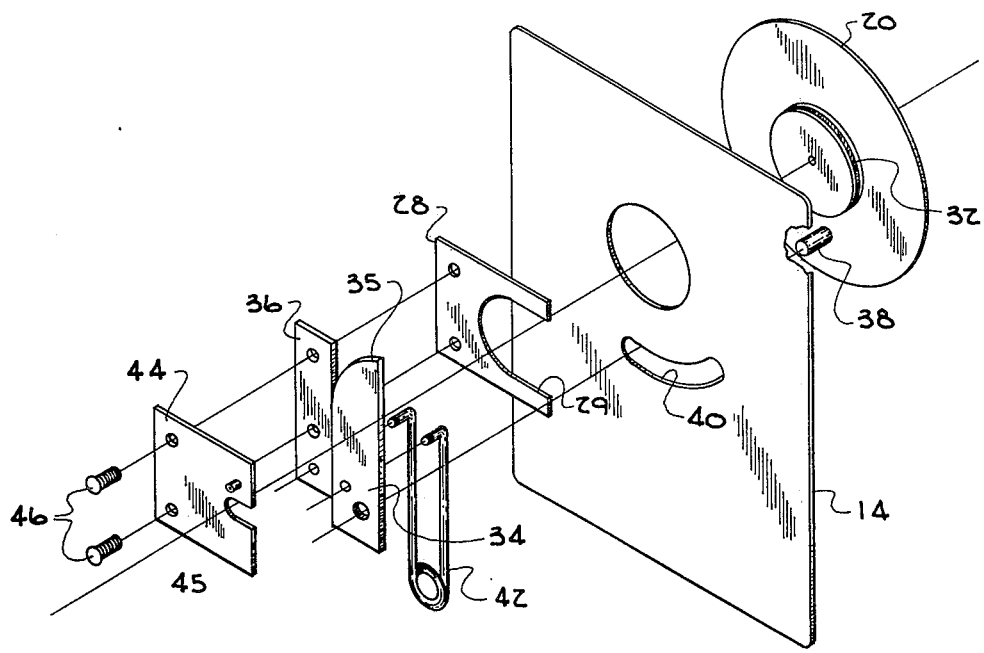
FIG. 4
FIG. 5
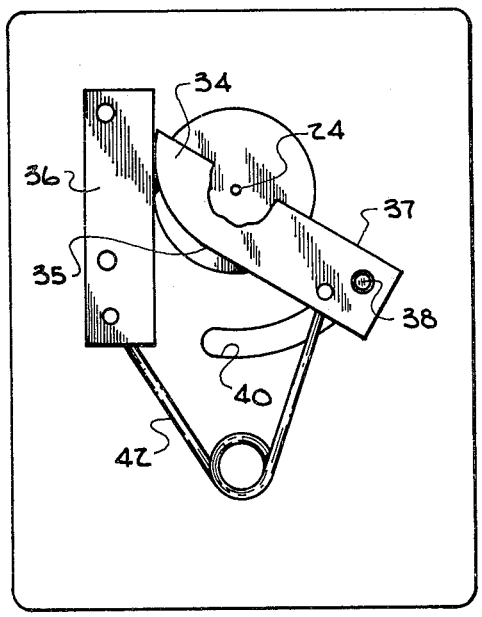
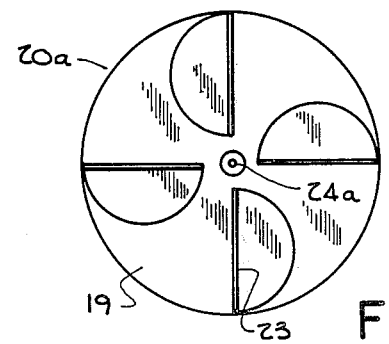
FIG. 6
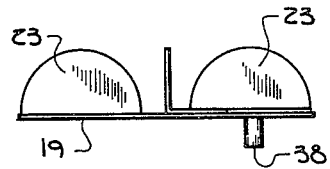
FIG. 7

4,315,448

HYPODERMIC NEEDLE DESTRUCTOR

BACKGROUND OF THE INVENTION

This invention relates to a device for destroying hypodermic needles. Today most injections are given with disposable hypodermic syringes which are supplied to hospitals and doctor's offices in sterile packages. Each hypodermic syringe is discarded after a single use so that there is no chance to cross-contaminate patients. In light of the numerous injections given today, this creates a substantial disposal problem. Accidental needle injuries to hospital personnel have become extensive due to the careless handling of the used syringes and creates a major health care problem. Even with specific instructions and careful handling their have been numerous injuries. Persons scratched by a used needle frequently do not know what kind of an injection or what illness the person had when the syringe was originally used. There have been a substantial number of persons who have become ill as a result of one of these needle-scratch incidents while initially it was not known that the illness was needle related.

In the prior art there have been a variety of destructor devices, such as U.S. Pat. No. 3,958,765, all of which basically pulverize the entire syringe into small pieces. Devices of this type are very substantial in size, since they require a very large motor and grinding unit, and therefore can only be located at one or two stations in a hospital. Utilizing a system of this type cannot prevent the injuries in handling between the point of use of the syringe and the central disposal site.

Another destructing device is disclosed in U.S. Pat. No. 3,404,593. While it is hand-operated, it does require a rather substantial structure and more complex operation than the very simplified unit of the present invention.

DESCRIPTION OF THE PRESENT INVENTION

Since the present invention is a very simple and inexpensive structure, the unit can be located at the precise location where the syringes are being used, namely the individual patient rooms, or other rooms where injections are given. The convenience of destroying needles at the point of use, obviates for the most part the previously mentioned scratch injuries. In considering the logistics of a hospital patient floor with a large number of beds, with patients requiring numerous injections at erratic times; the nursing staffs at present must return the used needles to a central location, after giving the injection, where they are collected and later destroyed. The needle destructor of the present invention can be very conveniently located on the wall of the patient room or emergency room, or in one of the more modern console devices used in individual rooms. The device would also have a substantial value for home use by individuals requiring insulin injections, thereby eliminating the possibilities of careless mishandling of the used syringes. The device of the present invention includes a receptacle which is an integral part of the device for collecting the sheared needles as they are separated from the syringes. These containers can be periodically emptied, or for additional capacity, they can be connected by a fixed pipe which will carry the cut needles to a larger capacity container.

It is therefore the principal object of the present invention to provide a simplified needle shearing device and collector point for the used needles.

Another object of the present invention is to provide a needle destructing device which can be wall-mounted at the precise location where syringes are used.

Another object of the present invention is to provide a disposal system which is completely sanitary and self-contained.

These and other objects of the invention will become more readily apparent upon further description with reference to the accompanying drawings, in which:

FIG. 1 is a perspective view of the hypodermic syring destructing device with a needle about to be inserted therein;

FIG. 2 is a rear elevational view of the shearing mechanism in the retracted position, taken along lines 2—2 of FIG. 3;

FIG. 3 is a side elevational section taken along line 3—3 of FIG. 2;

FIG. 4 is an exploded view of the cutting mechanism;

FIG. 5 is a rear elevational view of the mechanism in the extended position;

FIG. 6 is a plan view of a modified knob design; and

FIG. 7 is a side elevational view of the modified knob of FIG. 6.

DESCRIPTION OF THE PREFERRED EMBODIMENTS

Referring now to FIG. 1, there is shown a perspective view of the destructing device generally described by reference numeral 10. The device 10 includes a receptacle box 12 closed at its open end by a base plate 14, held in place by mounting screws 16 which are in turn threaded into mounting flanges 18 on receptacle box 12. The size of receptacle box 12 can be dimensioned the same as the standard electrical boxes so that the device can be readily mounted in the wall structure, along with other electrical juncture boxes. Pivotally mounted to the face plate 14 is a knob 20 with a recessed portion 22 in the center thereof. Radially spaced around the periphery of knob 20 are a series of raised ribs 21 which assist the operator in gripping and turning the knob 20. Located in the center of the recessed portion 22, is a small opening 24 for receipt of a hypodermic syringe needle 30. Opening 24 has a tapered section 26 which converges outwardly towards the receipt side of knob 20 so as to assist the user in inserting the syringe in the device.

The knob 20 is rotatably held in place by a clip 28, which is best seen in FIGS. 2, 3 and 4. Clip 28 includes a u-shaped opening 29, which slides laterally in place in the circumferential groove 32 surrounding the inside end of knob 20 after the end of knob 20 is inserted through base plate 14 (as seen in FIG. 4).

The shearing action of device 10 is brought about by rotational movement of knife blade 34. Knife 34 includes an arcuate camming surface 35, as best seen in FIGS. 2 and 5, which rotates across a stationary spacer member 36. The knife 34 includes a cutting edge 37 and an opening at its lower end for receipt of an actuating pin 38 which in turn is anchored to knob 20 and moves through an arcuate path indicated by slot 40 in base plate 14. Attached to spacer 36 and knife blade 34 is a tension spring 42 whose outer ends are bent at a 90° angle for receipt in holes in the respective members 36 and 34 for holding the knife blade in its retracted position, as viewed in FIG. 2. Positioned over knife blade 34 is a retainer plate 44 (not shown in FIG. 2) which limits the movement of knife blade 34 to the plane of its shearing action. Passing through retainer plate 44 is a small roll pin 45 which limits the upper end of knife blade 34 from any movement in a rightward direction, as viewed in FIG. 2. A pair of screws 46, as seen in FIG. 4, hold the clip 28, spacer 36 and retaining plate 44 in position against base plate 14.

FIG. 5 illustrates the position of the cutting knife in its fully extended position with the upper end of camming surface 35 resting upon spacer 36.

FIGS. 6 and 7 illustrate a modified form of the actuating knob fabricated from metal rather than molded plastic, as shown in FIG. 1. Welded to knob base 19 are four semicircular tabs 23 quadrangularly spaced around opening 24a, the tabs 23 are gripped by two fingers, somewhat like a conventional wing nut, as the handle is turned with the needle 30 inserted in shear opening 24a.

OPERATION

The shearing device 10 can be operated with one or two hands. The single hand method entails, first inserting the needle of the syringe, as seen in FIG. 1, into the shear opening 24, as far as possible until the shank of the needle contacts the knob. With the fingers of the same hand, the knob 20 is then gripped and rotated in a clockwise direction, as seen in FIG. 1. Since FIG. 2 is a rear view of the cutting mechanism, the knob 20 will move in a counterclockwise direction, as viewed in FIG. 2. Pin 38 connected to the back of knob 20 begins to swing knife blade 34 to the right, as viewed in FIG. 2, causing the cam surface 35 of the knife blade to roll across the fixed edge of spacer 36 until the right edge 37 of knife blade 34 comes in contact with the needle inserted in opening 24. The cutting edge 37 of knife blade 34 is not necessarily sharpened, however, it is made from tool steel and heat-treated to obtain a certain degree of hardness. Further movement of blade 34 across opening 24 will shear the needle, dropping into the bottom of retainer box 12. At rthe pont of shearing of the needle, the moment arm of the actuating knob 20 is more than twice the length of the shearing moment arm from the shearing opening 24 to the pivoting surface on spacer 36. This mechanical advantage of the actuating handle makes the handle force much reduced from that of a one-to-one ratio. After the blade 34 has sheared off the needle 30, and pin 38 has come to rest in the end of slot 40, the knob is released and spring 42 rotates knob 20 back to its fully retracted position, as seen in FIG. 2.

While the bottom of box 12 is shown closed, it can be modified to include a conduit 50, shown in dotted line, which would transmit the sheared needles to a larger pick-up container.

Having described the invention with sufficient clarity to enable those familiar with the art to construct and use it, I claim:

1. A hypodermic needle destructing device comprising:
    a receptacle;
    a base plate positioned on the front of the receptacle;
    a pivotally mounted knob on the base plate having an opening in the center thereof adapted to receive hypodermic needles;
    a knife blade means pivotally supported against the base plate approximate one end of the blade means;
    a slot in the base plate;
    pin means anchored to the knob passing through the slot in the base plate and pivotally attached to the opposite end of the knife blade whereby rotation of the knob causes the knife blade to pivot from its retracted position across said opening and shear the needle which is extending through said opening; and
    biasing means on the knife blade urging the blade toward its retracted position.

2. A hypodermic needle destructing device as set forth in claim 1, wherein the moment arm from the pin connection on the knife blade to the pivot point of the blade is at least twice the moment arm from the shearing point to the pivot point on the blade.

3. A hypodermic needle destructing device as set forth in claim 1, wherein the knife blade has a camming surface at the pivot point on the base plate and the base plate has a planar surface which the camming surface pivots against as it is rotated from its retracted to its shearing position.

4. A hypodermic needle destructing device as set forth in claim 1, wherein the receptacle includes a compartment for storing the sheared needles, and a closeable opening for removing the sheared needles.

5. A hypodermic needle destructing device as set forth in claim 1, wherein the knife blade has a camming surface at the pivot point on the base plate and the base plate has a planar surface which the camming surface pivots against as it is rotated by the pin means and the moment arm on the knife blade of the pin means is greater than the moment arm at the shearing point.

6. A hypodermic needle destructing device as set forth in claim 1, wherein the opening in said knob is cone-shaped, converging inwardly and terminating in an opening approximate the diameter of a standard hypodermic needle.

7. A hypodermic needle destructing device as set forth in claim 1, wherein the knob includes at least two gripping surfaces on the knob which are positioned radially and extend normal to the face of the knob whereby the knob can be actuated with two fingers.

8. A hypodermic needle destructing device as set forth in claim 1, wherein the knob includes a series of radially spaced ribs thereon to assist in gripping and turning a recessed portion in the center of the knob with the needle opening located therein to prevent accidental hand contact with the needle contact area.

* * * * *